United States Patent [19]

Verkuil

[11] Patent Number: 5,644,223

[45] Date of Patent: Jul. 1, 1997

[54] UNIFORM DENSITY CHARGE DEPOSIT SOURCE

[75] Inventor: Roger Leonard Verkuil, Wappingers Falls, N.Y.

[73] Assignee: International Business Machines Corporation

[21] Appl. No.: 440,502

[22] Filed: May 12, 1995

[51] Int. Cl.⁶ .......................... G01R 31/02; G01N 27/60
[52] U.S. Cl. ........................... 324/158.1; 324/455
[58] Field of Search ........................ 324/158.1, 455, 324/500, 501; 250/288, 281

[56] References Cited

U.S. PATENT DOCUMENTS

| | | | |
|---|---|---|---|
| 4,144,451 | 3/1979 | Kambara | 250/281 |
| 4,326,165 | 4/1982 | Szedon | 324/158 R |
| 4,663,526 | 5/1987 | Kamieniecki | 250/315 |
| 4,780,680 | 10/1988 | Reuter et al. | 324/455 |
| 4,812,756 | 3/1989 | Curtis et al. | 324/158 R |
| 5,051,583 | 9/1991 | Mimura et al. | 250/288 |
| 5,216,362 | 6/1993 | Verkuil | 324/158 D |
| 5,266,892 | 11/1993 | Kimura | 324/158 D |
| 5,267,555 | 12/1993 | Pajalich | 250/288 |
| 5,343,293 | 8/1994 | Berger et al. | 356/369 |

FOREIGN PATENT DOCUMENTS

| | | |
|---|---|---|
| 1122982 | 11/1984 | U.S.S.R. |
| 1796079 | 2/1993 | U.S.S.R. |

OTHER PUBLICATIONS

R. L. Verkuil, "Rapid Contactless Method for Measuring Fixed Oxide Charge Associated with Silicon Processing" IBM Technical Disclosure Bulletin, V. 24, No. 6, pp. 3048–3053, Nov. 1981.

M. S. Fung, et al, "Contactless Photovoltage vs Bias Method for Determining FLat–Band Voltage" IBM Technical Disclosure Bulletin, V.32, No.9A, pp. 14–17, Feb. 1990.

R. Hamers, et al, "High Spatial Resolution Measurement of Doping, Band–Bending, and Recombination at Semiconductor Surfaces" IBM Technical Disclosure Bulletin, V.33, No.1B, pp. 91–92, Jun. 1990.

Primary Examiner—Ernest F. Karlsen
Attorney, Agent, or Firm—Charles W. Peterson, Jr.; Graham S. Jones, II

[57] ABSTRACT

A method for measuring the thickness of very thin oxide layers on a silicon substrate. A corona discharge source repetitively deposits a calibrated fixed charge density on the surface of the oxide. The resultant change in oxide surface potential for each charge deposition is measured. By choosing a starting value for an assumed oxide thickness, the approximate change in silicon bandbending per corona discharge step is determined. The cumulative changes in bandbending versus oxide surface potential yields an experimental bandbending versus bias characteristic. A theoretical bandbending versus bias characteristic is established. The experimental and theoretical characteristics are matched at the predetermined points thereof and then the assumed oxide thickness is iterated until both characteristics superimpose in the silicon accumulation region. The iterated oxide thickness that allows both characteristics to superimpose is the oxide thickness value being sought. The finally evolved experimental characteristic also is used to determine the interface states density of the oxide. Specially designed corona discharge guns are described for use with the oxide thickness and interface states density measurement techniques.

8 Claims, 3 Drawing Sheets

UNIFORM DENSITY CHARGE DEPOSIT SOURCE

CROSS-REFERENCE TO RELATED APPLICATION

The specification and drawings of the present application are also contained within the simultaneously filed application, IBM Docket No. FI9-95-034, USPTO Serial No. 08/440,418, filed May 12, 1995, now U.S. Pat. No. 5,485,091, entitled "CONTACTLESS ELECTRICAL THIN OXIDE MEASUREMENTS" in the name of the present inventor and assigned to the present assignee.

BACKGROUND OF THE INVENTION

The present invention generally relates to techniques for measuring the thickness of thin insulating layers and associated oxide-silicon interface states charge density and, more particularly, to such measurements of very thin oxide layers of the order of 200 Angstroms and less and to corona discharge guns for use therewith.

Measuring the thickness of relatively thin oxides, DRAM storage node oxides, etc., normally can be done readily by optical or electrical instrumentation. For example, U.S. Pat. No. 5,343,293 issued to Rudolf Berger, et al. on Aug. 30, 1994, and the references cited therein, disclose optical ellipsometer means for measuring the thickness of oxide films on silicon wafers based upon a discernable change in polarized light passing through the film. The discernability or quantification of said change decreases sharply for reduced thicknesses of oxide films below about 200 Angstroms.

U.S. Pat. No. 4,780,680 issued to Klaus Reuter, et al. on Oct. 25, 1988 teaches a contactless electrical technique suitable for making approximate thickness measurements of relatively thick strips of insulating materials and insulating coatings such as tape and paint. Approximate oxide thickness measurements might be possible if the cited electrical technique were practiced on oxide layers on silicon. However, for reasons not explained in the patent but fully described hereinafter, the cited technique could not yield useful thickness results for oxide layers below about 200 Angstroms.

SUMMARY OF THE INVENTION

One object of the present invention is to provide an apparatus and procedure for making accurate thickness measurements on insulator layers on semiconductor substrates, said layers being very thin and as low as 40 Angstroms.

Another object is to provide a contactless electrical technique for measuring oxide layer thicknesses of less than about 200 Angstroms on a semiconductor substrate.

A further object is to provide a capacitance-voltage technique for measuring oxide layer thickness on a semiconductor substrate that corrects for the presence of non-zero accumulation bandbending effects (accumulation capacitance) in said substrate.

An additional object is to obtain accurate measurement of oxide layer thickness on a semiconductor substrate using a capacitance-voltage technique wherein the need is reduced to bias the oxide-silicon structure strongly into accumulation.

A further object is to provide a measure of the interface states density of insulating layers on semiconductor substrates, said layers having thicknesses as low as 40 Angstroms.

A still further object is to provide corona discharge guns suitable for use in the insulating layer thickness and interface states density measurement techniques of the present invention.

These and other objects of the present invention are achieved in a best mode embodiment by the provision of a corona discharge source for repetitively depositing a calibrated fixed charge density on the surface of a thin oxide layer on a silicon substrate. The resultant change in oxide surface potential for each charge deposition is measured with a vibrating probe. The invention recognizes that the change in oxide surface potential is due to the sum of the change in voltage across the oxide layer per se plus the change in silicon bandbending due to the presence of non-infinite accumulation capacitance in said substrate.

The oxide thickness measurement error that would be present, if the oxide surface potential were used without correction, is factored out mathematically by the use of the following successive approximation method. By choosing a starting value for the assumed oxide thickness and knowing the charge density deposited by each corona discharge burst, the approximate change in oxide voltage can be calculated. By subtracting this approximate change in voltage across the oxide from each experimentally derived change in oxide surface potential, the approximate change in silicon bandbending per corona discharge step can be determined. The cumulative change in bandbending versus oxide surface potential (oxide bias voltage) then yields an experimental bandbending versus bias characteristic. It should be noted that the starting assumed value for oxide thickness is taken from the change in oxide surface potential in the strong accumulation region of the aforesaid characteristic where the change in silicon surface potential is small enough to permit rough approximation of the oxide thickness.

A theoretical bandbending versus bias characteristic is established for a simulated ideal MOS device having the aforementioned assumed oxide thickness. No assumed value is made for any accumulation capacitance. The experimental bandbending versus bias characteristic then is compared to the theoretical bandbending versus bias characteristic. The two characteristics are matched at the points at which the second derivatives of each curve go through maximum values and then the assumed oxide thickness contributing to the shapes of both characteristics is iterated until both characteristics superimpose in the silicon accumulation region. The iterated oxide thickness that allows both characteristics to superimpose is the oxide thickness value being sought. The experimental bandbending versus bias characteristic finally evolved in accordance with the foregoing oxide thickness measurement technique also is used to determine the interface states density of the specimen oxide layer. Specially designed corona discharge guns are provided for use with the insulating layer thickness and fast states density measurement techniques.

BEST MODE FOR CARRYING OUT THE INVENTION

Silicon accumulation capacitance, e.g., that effective capacitance which extends below the interface between a charged oxide layer and an underlying silicon substrate, can be ignored when making thickness measurements of relatively thick insulating layers where the layer thickness is very many times greater than the depth of any accumulation layer. Silicon substrate accumulation capacitance is in series with oxide layer capacitance and is normally high enough to be considered as essentially infinite when compared to oxide layers that are thicker than about 200 Angstroms. Below 200 Angstroms, the accumulation capacitance becomes appreciable relative to oxide capacitance and can not be ignored. Moreover, when the oxide layer thickness becomes as low as 40 Angstroms, as in the evolving state of the art for CMOS and DRAM technology, the electrical fields that can be used to bias the MOS structure into accumulation must be kept lower than for thicker oxides (to avoid tunnelling problems). Therefore, the MOS structures cannot be biased as strongly into accumulation which, in turn, reduces the silicon accumulation capacitance and makes the error of the conventional electrical thickness measurements even greater where accumulation capacitance is ignored.

Figure 1:
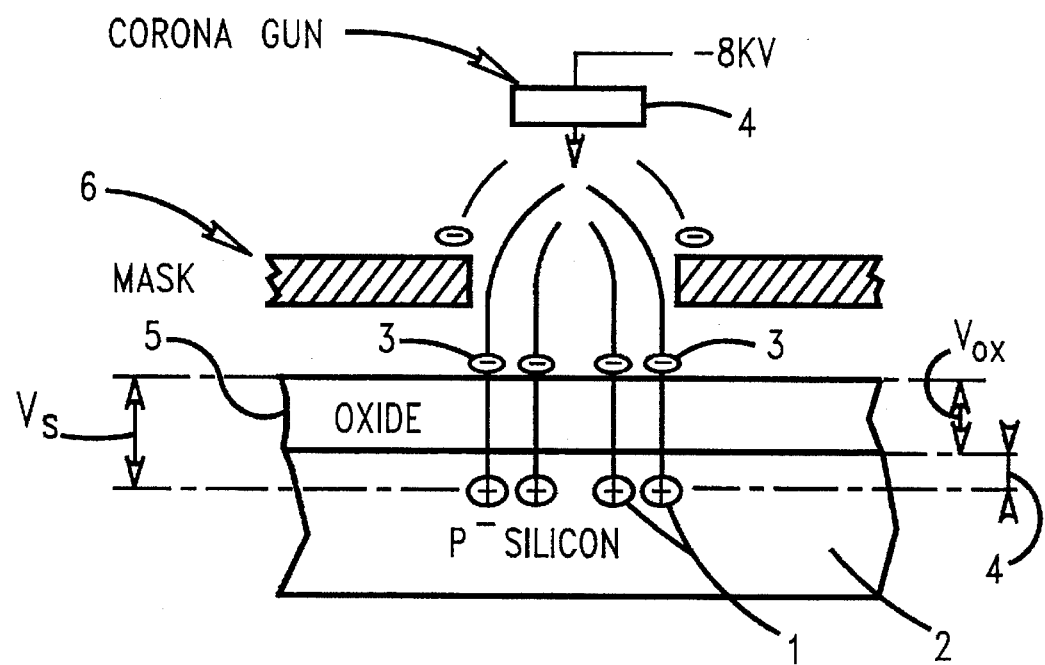
FIG. 1 is an idealized cross-sectional view of the electric field pattern existing within a specimen whose oxide layer thickness is being measured in accordance with the present invention.

Referring to FIG. 1, positive charge accumulation 1 in P-silicon substrate 2 results from the deposition of negative charges 3 from negative corona discharge gun 4 onto the surface of oxide layer 5 overlying substrate 2. The corona discharge is applied to the area of interest via mask 6. It is necessary for purposes of obtaining accurate thickness measurements, that a uniform density of charge 3 be deposited through the aperture in mask 6. A specially constructed corona discharge gun for achieving such uniformity will be described later in connection with FIG. 3a.

Returning again to FIG. 1, it will be noted that the potential measured at the upper surface of oxide layer 5 ($V_s$) relative to the bulk of substrate 2, is the sum of the voltage drops across oxide 5 (Vox) and across the space charge region between the lower surface of oxide layer 5 and the level of the accumulated charges within substrate 2 ($\Psi$). Thus, Vs=Vox+$\Psi$. The functional relationship between the deposited charge Q and the resultant voltage $\Psi$ is described by equations (13) and (16) in the book "Physics of Semi-Conductor Devices" by S. M. Sze, John Wiley and Sons, 1981, pp 366–369. When a value is assumed for the thickness of oxide 5 and there are known values for the deposited charge density 3, dielectric constant of oxide 5 and the P-dopant level of substrate 2, a theoretical value for $\Psi$ may be calculated. When it is further assumed that a succession of equal valued charges are deposited upon the surface of oxide 5, the corresponding theoretical values for $\Psi$ may also be calculated and plotted. Such a theoretical plot (theoretical bandbending vs bias voltage characteristic) is shown by curve 7 of FIG. 2a.

In order to determine the thickness of the oxide layer of a portion of a specimen conforming to the oxide covered silicon substrate structure of FIG. 1, in accordance with the present invention, a succession of experimentally derived second curves are compared with the theoretical plot. A first of such a succession of experimental plots (experimental bandbending vs bias voltage characteristics) is represented by the curve 8 of FIG. 2a. Curve 8 first must be indexed, relative to curve 7, so that the silicon accumulation regions of each may be conveniently compared to each other. This is achieved by determining the point at which the second derivative of each curve goes through a maximum value and then translating the experimental curve until its maximum second derivative point closely coincides with the maximum second derivative point of the theoretical curve. It can be seen from FIG. 2a that experimental curve 8 accordingly is to be translated an amount $\Delta_1$ along the Q abscissa and an amount $\Delta_2$ along the $\Psi$ ordinate to achieve the required indexing. Curve 8' shows the result of translating curve 8 by an amount $\Delta_2$. Curve 8' also is to be translated by the amount $\Delta_1$.

Figure 2C:
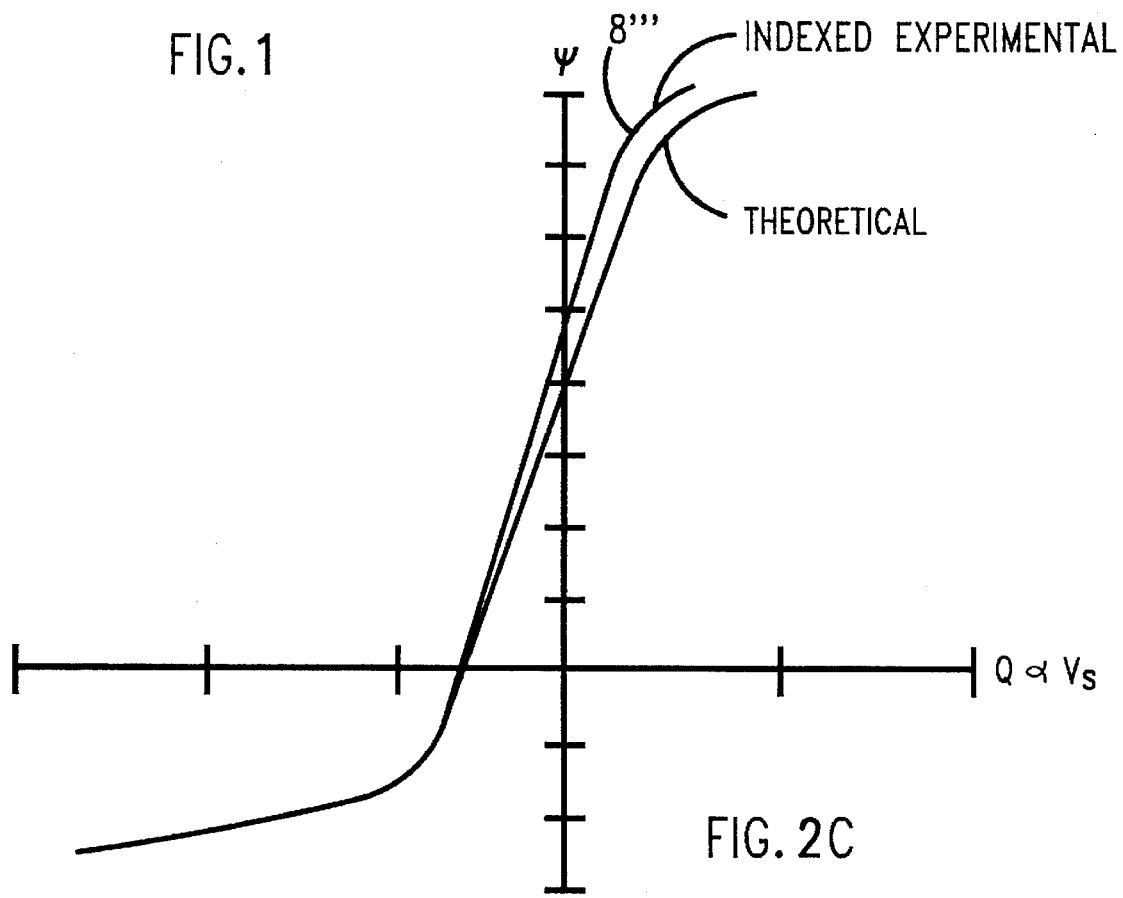
FIGS. 2a–2c are a partial set of theoretical and experimental bandbending versus bias characteristics being iteratively indexed and compared to each other.
Figure 2A:
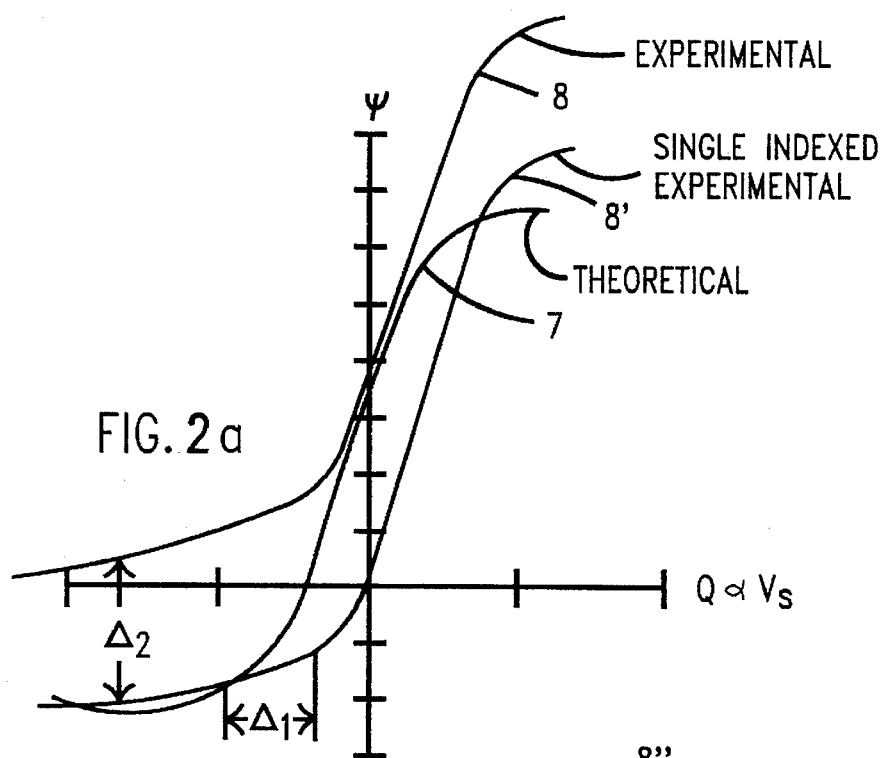
Figure 2B:
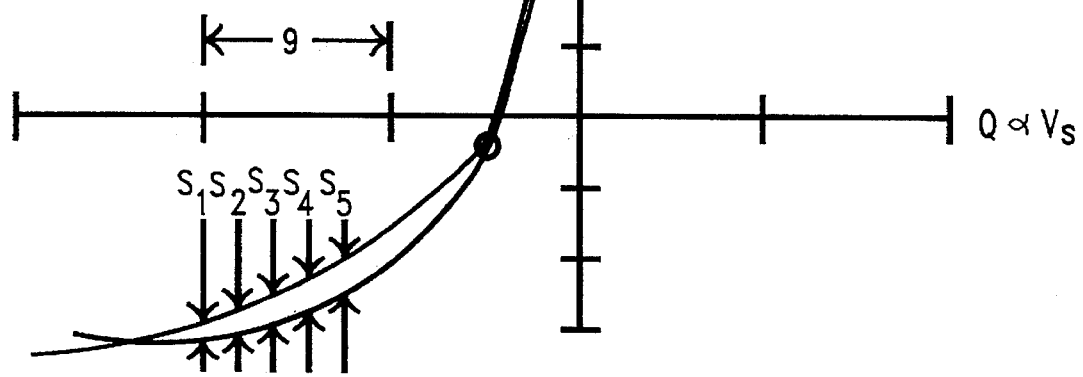

FIG. 2b depicts the result of the aforedescribed double indexing of curve 8 of FIG. 1 to yield curve 8" of FIG. 2b. It should be noted that the actual comparison of curves 7 and 8" takes place within the region 9 corresponding to when the substrate 2 of FIG. 1 is placed into an accumulation status by deposited charges 3. The entire curve 8 is produced by a succession of about 20 equal charge bursts from corona gun 4, five of which bursts occur over the region 9. The resulting twenty data samples, i.e., the voltage changes between the top surface of the oxide layer and the bulk of the semiconductor substrate, are measured by a vibrating Kelvin probe apparatus (not shown) such as is described, for example, in U.S. Pat. No. 4,812,756 issued to Huntington W. Curtis et al. on Mar. 14, 1989 and assigned to the present assignee. Curve fitting techniques are used to smooth the corresponding points on the $\Psi$ vs Q characteristic so that a continuous curve such as curve 8 is produced after all 20 voltage data samples have been taken.

Curves 7 and 8" are compared at sampling locations $S_1$ to $S_5$ and, if any difference exists, a new incremented value for the assumed oxide thickness parameter is chosen. Using the same measured values as before but incrementing the initially assumed value for oxide layer thickness, the entire computational process is iterated to yield a new experimental curve for each assumed thickness value until comparison with the theoretical curve shows a match. Eventually, the indexed experimental curve and the theoretical curve will become properly matched as shown in FIG. 2c. The assumed oxide thickness that finally allows both characteristics to superimpose properly, as shown in FIG. 2c, is the oxide thickness value being sought, i.e., the true thickness value of the oxide layer on the specimen undergoing measurement.

To generate the initial experimental characteristic and to carry out the comparison and then to generate the iterated additional experimental characteristics and to carry out the additional comparisons required to ascertain oxide layer thickness takes about 3 minutes on an automatic computer controlled tester.

The experimental and the theoretical bandbending versus bias characteristics of FIG. 2c finally evolved in accordance with the foregoing oxide thickness measurement technique also can be used to determine the interface states density of the specimen oxide. In this case, the slope of said experimental bandbending versus bias is compared against the slope of the theoretical ideal bandbending characteristic at a number of different values of $\Psi$. More particularly, the slopes of the curves of FIG. 2c are compared at a number of different $\Psi$ value points to yield corresponding interface states density values in accordance with the expression:

$$N_{ss}(\Psi) = \frac{1}{q} \left[ \left. \frac{dQ_{ox}}{d\Psi} \right|_{EXP} - \left. \frac{dQ_{si}}{d\Psi} \right|_{IDEAL} \right]$$

where:

$N_{ss}$=interface states density* q=unit charge per electron $$\frac{dQox}{d\psi} = \text{slope of experimental curve 7}$$

at a given value of $\Psi$ $$\frac{dQsi}{d\Psi} = \text{slope of ideal curve at said given value of } \Psi$$

* in more recent literature, the symbol for interface states is $D_{it}$.

The above expression is readily derived from equation (2) of the paper *Surface States at Steam-Grown Silicon-Silicon Dioxide Interfaces* by C. N. Berglund, IEEE Transactions on Electron Devices, Vol. ED-13, No. 10, October 1966, p. 701.

To do such an interface states measurement, the exact flatbending characteristic needs to be known because that characteristic, as derived in the oxide thickness measurement, includes an offset term. This offset term could be conveniently determined by also taking photovoltage measurements, along with each oxide surface potential data point, and noting the bias voltage where the photovoltage went to zero. This should be a more accurate method for determining bandbending versus bias characteristics, in comparison to observing photovoltage versus bias characteristics and attempting to convert the photovoltage versus bias characteristics into bandbending versus bias characteristics.

Figure 3A:
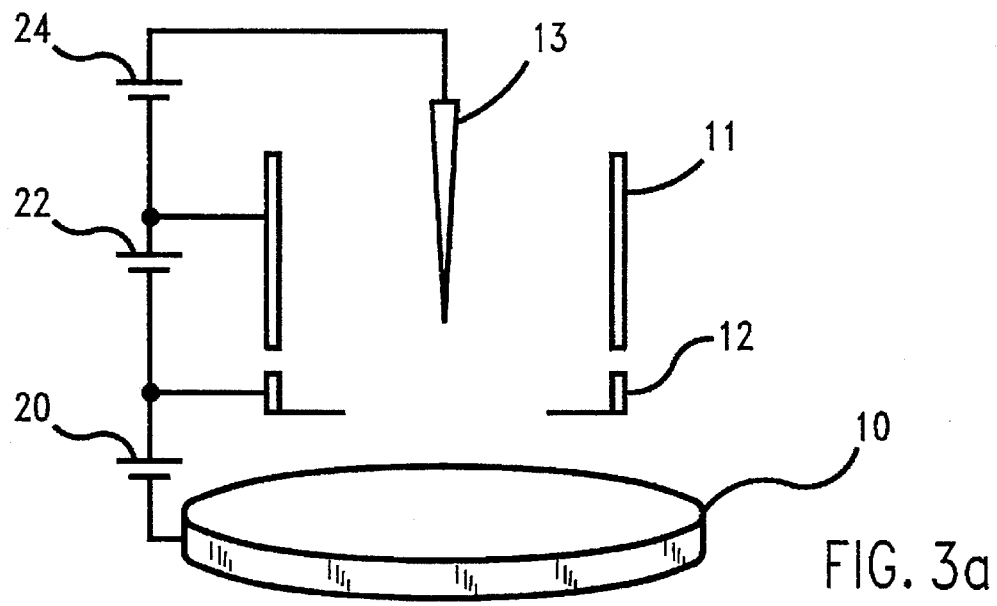
FIGS. 3a and 3b are simplified cross-sectional views of corona discharge sources for depositing a repetitively uniform fixed charge density across an area of interest of an oxide layer whose thickness alone or together with interface states density are to be measured.

FIG. 3a is a simplified cross-sectional view, partly in perspective, of the best mode embodiment of the corona discharge gun used in the oxide thickness measurement aspect of the present invention. Considerations to be taken into account in the design of the gun include providing a well-defined and substantial beam charge density (to minimize measurement time) having relative uniformity (for measurement accuracy) across the selected oxide-coated site of interest on wafer 10. Typical prior art point (needle-to-plane) sources omitting beam shaping electrodes 11 and 12 about needle 13 of FIG. 3a are not suitable. A high voltage (typically + or −6 to 9 kilovolts) is applied to the prior art needle relative to the wafer site. Positive or negative ionized molecules are generated at the needle tip which then follow the electric field lines from the tip of the needle down to the wafer. In the absence of beam shaping electrodes 11 and 12 and the bias voltages applied thereto of the present invention, the corona charge density impinging on the wafer site is highest immediately under the needle and diminishes rapidly with increasing radial distance from the axis of the needle. Such broad area, non-uniform charging is not suitable for obtaining accurate oxide thickness measurements or interface states measurements at the wafer site.

The addition of beam shaping electrodes 11 and 12 concentric with the axis of needle 13 and the biasing voltages 20, 22 and 24 applied thereto of FIG. 3a improves the corona charging capability of the gun in two important ways. Firstly, lower electrode 12 acts as a mask for defining the diameter of the area of corona deposition. Secondly, the bias voltage on electrode 12 (same polarity as the corona ions) repels ions that normally would be captured by the edge of electrode 12 and directs them down to the wafer site with an enhanced density that abruptly ceases under the edge of electrode 12. The upper electrode 11 helps to boost the efficiency of the corona gun by being biased at a relatively high voltage (up to ±3 kilovolts) with the same polarity as the corona ions. Potentials in the range of ±6–9 KV and up to ±1.5 KV are appropriate for needle 13 and mask electrode 12, respectively. This results in an electric field configuration, in the upper region of the corona source, that prevents many of the ions from being captured by the upper electrode and directs them down to the lower electrode 12 which, in turn, directs them to the wafer site. It should be noted that needle 13 and electrodes 11 and 12 are supported and insulated from each other by suitable insulated support members (not shown) that allow for the application of the necessary biases.

Figure 3B:
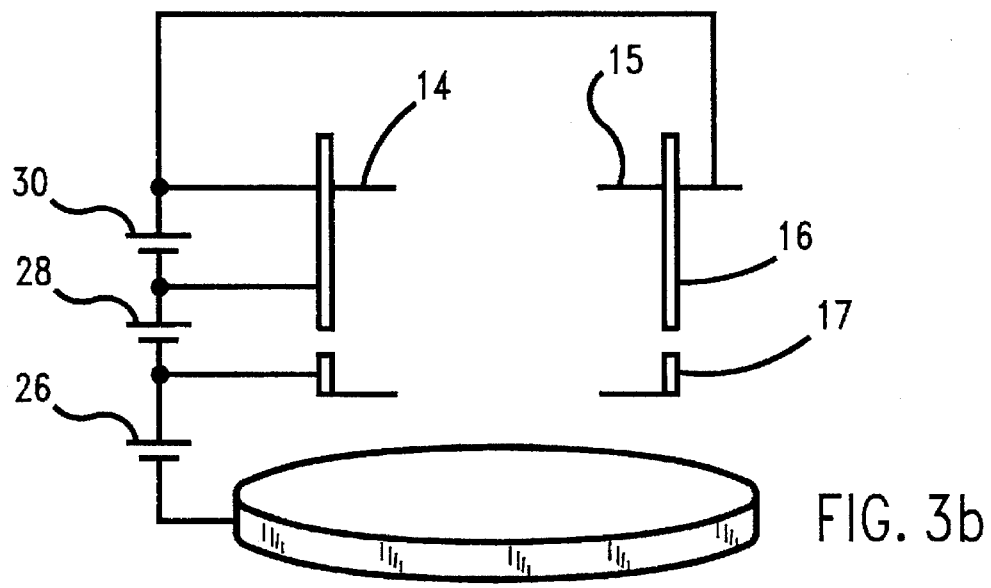

FIG. 3b is a simplified cross-sectional view, partly in perspective, of the best mode embodiment of the corona discharge gun used in the oxide charge measurement aspect of the present invention. In order to use a corona discharge source for non-contact measurement of oxide charges at selected wafer sites, it is essential that the source very uniformly deposits charges on an insulating (oxide) surface. As previously pointed out, typical point (needle) to wafer site sources are not able to do this. Although a substantial improvement in uniformity of deposited charges is achieved with the addition of the beam shaping electrodes and voltages discussed in connection with FIG. 3a, even more uniformity is desired for oxide charge measurements and interface states charge measurements than in the case of oxide thickness measurements This is due to the fact that there is increased sensitivity to deposited charge non uniformity when making the slope comparison required for the interface states measurement than when making the oxide thickness measurement, inasmuch as two distinctly different regions of the finally evolved bandbending versus bias characteristic are involved in the two cases. Moreover, the small degree of the remaining non-uniformity associated with the gun of FIG. 3a is typically not the same for both positive and negative corona either of which might be needed in a given measurement case. This undesired asymmetry in plus and minus corona is greatly minimized using the gun configuration of FIG. 3b.

FIG. 3b is essentially the same as FIG. 3a except for the important difference that two facing and horizontal needles 14 and 15 are provided in FIG. 3b in lieu of the single vertical needle 13 of FIG. 3a. The potentials 26, 28 and 30 applied to the needles 14 and 15 and electrodes 16 and 17 of FIG. 3b may be the same as of the corresponding parts in the case of FIG. 3a.

The mechanism is not precisely known that causes the gun of FIG. 3b to deliver more uniform deposited charges, however, the following heuristic explanation is offered.

In the case of FIG. 3a, ions travel directly down to the wafer site from the point of ionization at the tip of the needle. However, if the localized generation of ions about the tip of the needle is not uniform, then the flux of ions down to the wafer site will not be uniform. Furthermore, if the localized generation of positive and negative ions does not occur at precisely the same physical location about the tip of the needle, then the charging flux of positive and negative ions will be asymmetric. These non-uniformity and asymmetrical charging problems could possibly be explained by FIG. 3a providing very little opportunity for the ion flux to become more homogenous, prior to impinging on the wafer surface. In contrast, in FIG. 3b, the ions generated at the tip of the needles do not travel directly down to the wafer surface, since they are first directed toward the walls of the upper beam shaping electrode 16. Instead, these ions tend to be repelled from the upper electrode and are then, very likely, caught up in a swirling air pattern (normally referred to as "electric wind" in corona discharge literature). The electric wind can be viewed as the product of increased air pressure immediately in front of the needle tip, due to ions being repelled from the tip, which then creates a region of reduced pressure upstream from the tip. This results in a swirling action. Since the ions are not immediately directed downward to the wafer site, there is time for this swirling effect to make the ion population more uniform before it impinges upon the wafer surface. More broadly, the swirling effect can be produced using one or more needles having non-vertical orientations whereby the ions are initially directed at the walls of the upper electrode 16 rather than at the wafer surface.

A disadvantage of the gun of FIG. 3b, relative to that of FIG. 3a, is that the more indirect paths for the ions in the case of FIG. 3b results in a lower charging density. This translates to a longer time than necessary to complete the oxide thickness measurement where the increased uniformity of the deposited charges from the gun of FIG. 3b is not essential. This is why the gun of FIG. 3a is preferred if only an oxide thickness measurement is desired and not an interface states measurement as well.

While the present invention is described in terms of preferred embodiments, it is understood that numerous variations and modifications will occur to a person skilled in the art without departing in spirit from the claimed invention. It is intended that the scope of the claims include those modifications and variations that fall within the spirit of the invention.

What is claimed is:

1. A device including a corona discharge gun having a longitudinal, vertical axis and a transverse axis intersecting said longitudinal axis, said gun comprising at least one transversely oriented, biased needle-shaped electrode providing a source of ions of a given polarity at the tip of each said at least one needle-shaped electrode,
   a biased focusing ring electrode, and
   a biased masking electrode, said masking electrode comprising a centrally apertured disk,
   said electrodes being insulated from each other and supported so that said ring electrode and said apertured disk are mutually coaxial with said vertical axis,
   said ring electrode being positioned intermediate to each said tip and said masking electrode.

2. The device described in claim 1 wherein said ring and said masking electrodes are biased with a voltage having the same polarity as the polarity of said ions.

3. A device including a corona discharge gun adapted for interacting with a work piece positioned at a work piece location, said gun including a first transverse axis and a second, vertical axis, said first axis and said second axis being substantially perpendicular to each other,
   a biased focusing ring, beam-shaping electrode having beam shaping walls,
   said gun comprising two biased co-axial needle-shaped electrodes spaced apart, and aligned along said first transverse axis, the tips of said needle-shaped electrodes facing each other and facing said beam-shaping walls and providing a source of ions of a given polarity,
   said biased, focusing ring, beam-shaping electrode having said second, vertical axis as the axis thereof perpendicular to the plane of said ring, a space defined within said beam-shaping electrode, said tips of said needle-shaped electrodes extending within said space within said beam-shaping electrode, and
   a biased masking electrode, said masking electrode comprising a centrally apertured disk located between said needle shaped electrodes and said work piece location,
   said electrodes being insulated from each other, and said electrodes being supported, so that said focusing ring, beam-shaping electrode and said apertured disk of said masking electrode are coaxial along said second, vertical axis,
   said ring and said masking electrodes being biased with a voltage having the same polarity as the polarity of said ions,
   said first axis and said second axis being perpendicular relative to each other and said first axis intersecting said second axis centrally between said facing tips of said needle-shaped electrodes so ions generated at the tip of said needle-shaped electrodes are first directed at said beam-shaping walls of said beam shaping electrode before travelling down to the surface of said work piece, and
   said ring electrode being positioned intermediate said facing tips and said masking electrode.

4. A device including a corona discharge gun adapted for interacting with a work piece positioned at a wafer,
   said gun including a first transverse axis and a second, vertical axis, said first axis and said second axis being substantially perpendicular to each other,
   a biased, beam-shaping electrode having beam-shaping walls defining a beam-shaping space,
   said gun comprising two biased co-axial needle-shaped electrodes spaced apart, and aligned along said first transverse axis, the tips of said needle-shaped electrodes facing each other and facing said beam-shaping walls and providing a source of ions of a given polarity,
   said beam-shaping electrode having said second, vertical axis as the axis thereof perpendicular to the plane of said ring,
   said tips of said needle-shaped electrodes extending within said beam-shaping space within said beam-shaping walls of said beam-shaping electrode, and
   a biased masking electrode, said masking electrode comprising a thin, centrally apertured disk located between said needle shaped electrodes and said wafer,
   said electrodes being insulated from each other, and said electrodes being supported, so that said beam-shaping electrode and said apertured disk of said masking electrode are coaxial along said second, vertical axis,
   said ring and said masking electrodes being biased with a voltage having the same polarity as the polarity of said ions,
   said first axis and said second axis being perpendicular relative to each other and said first axis intersecting said second axis centrally between said facing tips of said needle-shaped electrodes so ions generated at the tip of said needle-shaped electrodes are first directed at said beam-shaping walls of said beam-shaping electrode before travelling down to the surface of said wafer, and
   said ring electrode being positioned intermediate said facing tips and said masking electrode,
   whereby ions are directed from said beam-shaping electrode towards said wafer through said masking electrode.

5. The device described in claim 1 wherein said disk is thin.

6. The device described in claim 2 wherein said disk is thin.

7. The device described in claim 3 wherein said disk is thin.

8. The device described in claim 4 wherein said thin disk of said masking electrode comprises a round flat plate with a central aperture.

* * * * *